United States Patent
Shah

(10) Patent No.: US 7,489,973 B2
(45) Date of Patent: Feb. 10, 2009

(54) APPARATUS AND METHOD FOR ALLEVIATING NAUSEA

(76) Inventor: Kamlesh Babulal Shah, 2 Hillcrest Ct., Burr Ridge, IL (US) 60527

(*) Notice: Subject to any disclaimer, the term of this patent is extended or adjusted under 35 U.S.C. 154(b) by 190 days.

(21) Appl. No.: 11/088,406

(22) Filed: Mar. 24, 2005

(65) Prior Publication Data

US 2006/0217786 A1    Sep. 28, 2006

(51) Int. Cl.
- A61N 1/04 (2006.01)
- A61N 1/08 (2006.01)
- A61H 39/00 (2006.01)

(52) U.S. Cl. ................ 607/149; 128/907
(58) Field of Classification Search ........ 128/907; 607/149; 600/548; 606/189, 204, 41–48, 606/129

See application file for complete search history.

(56) References Cited

U.S. PATENT DOCUMENTS

| | | | |
|---|---|---|---|
| 4,981,146 A | 1/1991 | Bertolucci | 128/802 |
| 6,361,550 B2 | 3/2002 | Grey | 606/204 |
| 6,382,215 B1 | 5/2002 | Morrish | 128/898 |
| 6,567,695 B1 | 5/2003 | Gruzdowich | 607/2 |
| 2002/0156501 A1 | 10/2002 | Grey | 607/2 |
| 2003/0069627 A1* | 4/2003 | Giuntoli et al. | 607/149 |
| 2003/0195585 A1* | 10/2003 | Gruzdowich et al. | 607/45 |

OTHER PUBLICATIONS

Kwang Il Shin, Dong Soo Kim, Keon Sik Kim, Young Suk Kim. Effect of Electric Acupuncture Stimulation of PC 6 and PC 7 Antiemetic Point on Postoperative Nausea and Vomiting. Korean J Anestheisol Mar. 1995; 028(03): 433-439.*
Translation of: Kwang Il Shin, Dong Soo Kim, Keon Sik Kim, Young Suk Kim. Effect of Electric Acupuncture Stimulation of PC 6 and PC 7 Antiemetic Point on Postoperative Nausea and Vomiting. Korean J Anestheisol Mar. 1995;028(03): 433-439.*

* cited by examiner

Primary Examiner—Carl H. Layno
Assistant Examiner—Tammie K. Heller
(74) Attorney, Agent, or Firm—Ash Tankha

(57) ABSTRACT

A method and apparatus for prevention and treatment of nausea and vomiting by the simultaneous electrical stimulation of the pericardium meridian six point and pericardium meridian seven point on the ventral side of the wrist of a patient. The meridian stimulator comprises a wrist-band like housing that is worn on the ventral side of the human wrist and contains a circuitry means included within the said housing and electrically coupled to the electrodes. A negative electrode is positioned on the pericardium meridian six point and a positive electrode is placed on the pericardium meridian seven point and a low amperage current is passed through these points via electrodes positioned at these points. A liquid crystal display unit reads the current supplied to the electrodes and indicates via an indicator light when current is being supplied to the meridian stimulator and further comprises a touch screen for a power on and off button and for increasing the rate of electrical stimulations.

14 Claims, 5 Drawing Sheets

APPARATUS AND METHOD FOR ALLEVIATING NAUSEA

BACKGROUND OF THE INVENTION

Nausea and vomiting are typically induced following the administration of general anesthesia and certain drugs, for example, narcotic pain alleviation and chemotherapy drugs. Also, conditions such as vertigo, dizziness, tinnitus, motion sickness and sea-sickness cause nausea. Anti-nausea remedies currently available in the market today include anti-nausea drugs, chemotherapy, acupuncture, acupressure and electro-acupuncture.

Stimulation of various areas on the body is known to be an effective treatment method for various medical conditions. Acupuncture and acupressure are existing Chinese therapeutic techniques that involve the stimulation of certain meridians and small, finite size points on the meridians known as acupuncture points. The current acupressure treatment for the alleviation of nausea and vomiting induced by general anesthesia, narcotic pain medications, chemotherapy, vertigo, dizziness, tinnitus and motion sickness consists of stimulation of an acupuncture point on the pericardium meridian known as the PC 6 point in a single therapeutic session.

Electro-acupuncture devices use non-invasive point stimulation whereby electricity is passed through two electrodes along the acupuncture meridians or channels. An example of an electro-acupuncture device is an electrode housed in a wrist-band that is positioned on the PC 6 acupuncture point and powered by a local battery to energise the PC 6 acupuncture point of the patient for the relief of nausea and vomiting. When administered properly, electro-acupuncture devices generally cause no physical injury to the patient and provide a non-chemical, non-invasive, painless and inexpensive method of alleviating nausea.

This invention comprises the stimulation of two acupuncture points on the pericardium meridian on the ventral side of the wrist known as the pericardium meridian six point (PC 6) and pericardium meridian seven point (PC 7) by the application of an electrically generated stimulus by a negative electrode positioned on the PC 6 point and a positive electrode positioned on the PC 7 point. The PC 6 acupuncture point is located on the pericardium meridian between the palmaris longus and flexor capri radialis tendons on the PC 3 and PC 7 line. The PC 7 point is located on the pericardium meridian at the middle of the wrist crease between palmaris longus and flexor carpi radialis tendons. It was found that the simultaneous electrical stimulation of both PC 6 and PC 7 is much more effective for the prevention and treatment of nausea and vomiting compared to the stimulus of the area around only the PC 6 point.

DETAILED DESCRIPTION OF THE INVENTION

Figure 1:
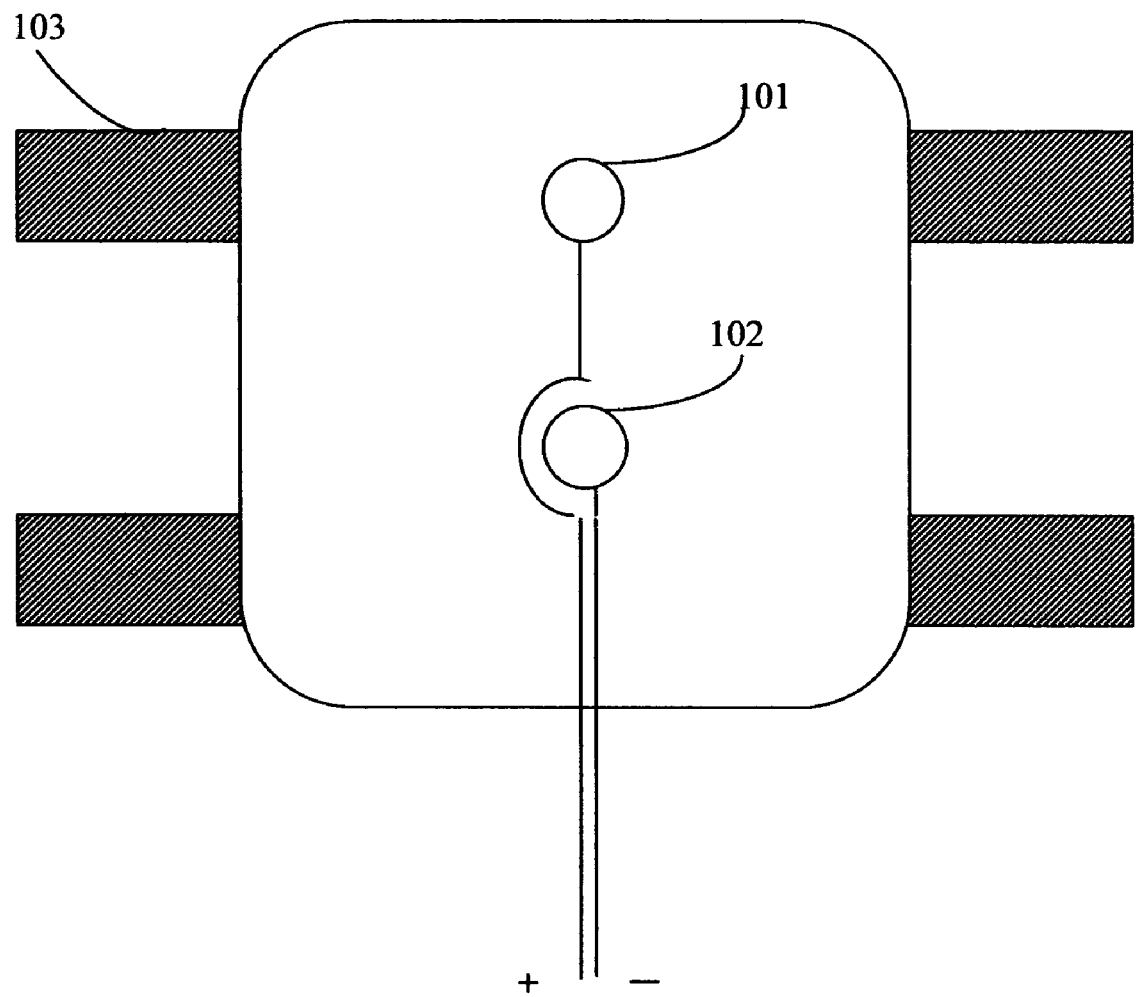
FIG. 1 illustrates the electrodes in the pericardium meridian stimulator for the prevention and treatment of nausea and vomiting.

FIG. 1 illustrates the position of the electrodes in the pericardium meridian stimulator 200 used for prevention and treatment of nausea and vomiting. The positive electrode 101 and the negative electrode 102 housed within the pericardium meridian stimulator 200 are powered by a local battery to provide a pulsed or a continuous electro-stimulation signal at the PC 6 and PC 7 points.

The positive electrode 101 and negative electrode 102 are made of an electrically conducting material. In one embodiment of the invention, the electrodes are coated with a gel during manufacture of the pericardium meridian stimulator 200 and a removable plastic sheet is placed over the gel to hold the gel in place. Prior to the use of the pericardium meridian stimulator 200, the medical practitioner peels the plastic sheet off the electrodes 101 and 102 and positions the electrodes that are covered by a layer of gel on the pericardium meridian points PC 6 and PC 7 on the wrist 303 of the patient. In another embodiment of the pericardium meridian stimulator, the gel is not provided with the electrodes during the assembly of the pericardium meridian stimulator 200 but is applied on the electrodes before the electrodes are positioned on the PC 6 and PC 7 points of the patient 303. The positive electrode 101 and the negative electrode 102 are electrically insulated from each other. The bottom of the pericardium meridian stimulator 200 is made of an electrically insulating material, for example, a plastic.

The spacing between the pericardium meridian six point (PC 6) 301 and pericardium meridian seven point (PC 7) 302 varies with age and body structure. To accommodate this variance, the present invention allows the relative movement and positioning of one electrode with respect to the other electrode along a guide or track in the housing of the pericardium meridian stimulator 200.

In one embodiment of the invention, the position of the positive electrode 101 is fixed with respect to the negative electrode 102 in the pericardium meridian stimulator with the position of negative electrode 102 adjustable along the longitudinal axis of the pericardium meridian defined by the line connecting points PC 6 and PC 7. The positive electrode 101 is positioned on the PC 7 point 302 and the negative electrode 102 is positioned on the pericardium meridian six point (PC 6) 302 via a distance adjustment means, for example, a guide or track in the housing along which the negative electrode 102 can move.

In another embodiment of the invention, the position of the negative electrode 102 is fixed with respect to the positive electrode 101 in the pericardium meridian stimulator with the position of positive electrode 101 adjustable along the longitudinal axis of the meridian defined by the line connecting points PC 6 and PC 7. Electrode 102 is positioned on the PC 6 point 301 and the position of the positive electrode 101 is positioned on the pericardium meridian seven point (PC 7) 302 via a distance adjustment means, for example, a guide or track along which the positive electrode 101 can move.

The pericardium meridian stimulator 200 includes a wristband like housing that contains a strap 103 for strapping the pericardium meridian stimulator 200 onto the wrist of the patient. The housing of the pericardium meridian stimulator 200 which holds the electrodes and electrical circuitry is made of an electrically non-conductive material, for example, a plastic. The strap 103 is also made of an electrically non-conductive material. The strap 103 is flexible and is made of either adhesive packing or Velcro®, thereby allowing non-invasive contact of the pericardium meridian stimulator 200 with the body.

The positive electrode 101 and the negative electrode 102 are located on the lower surface of the pericardium meridian stimulator 200 and in indirect contact with the patient's skin through the gel medium. The positive electrode 101 and the negative electrode 102 are detachably attached to the housing. The battery 208 and the control electronics are located in the housing of the pericardium meridian stimulator 200. When electric power is supplied to the positive electrode 101 and to the negative electrode 102, the pericardium meridian points PC 6 301 and PC 7 302 are simultaneously stimulated.

The positive electrode 101 and the negative electrode 102 are each coupled via an electrical connector on the electrical circuit to the battery 208 located in the pericardium meridian stimulator 200. The electrically conducting sheath around the positive electrode 101 and the negative electrode 102 and the straps 103 are disposable. The electrically conducting sheath is fabricated from a polymer conducting material, for example a material comprising a metal bonded or impregnated to a polymer. In another embodiment of the invention, the sheath comprises a mesh or foil constructed of a high conductivity metal, for example silver, copper, etc. The LCD and electric circuit assembly are non-disposable.

Figure 2A:
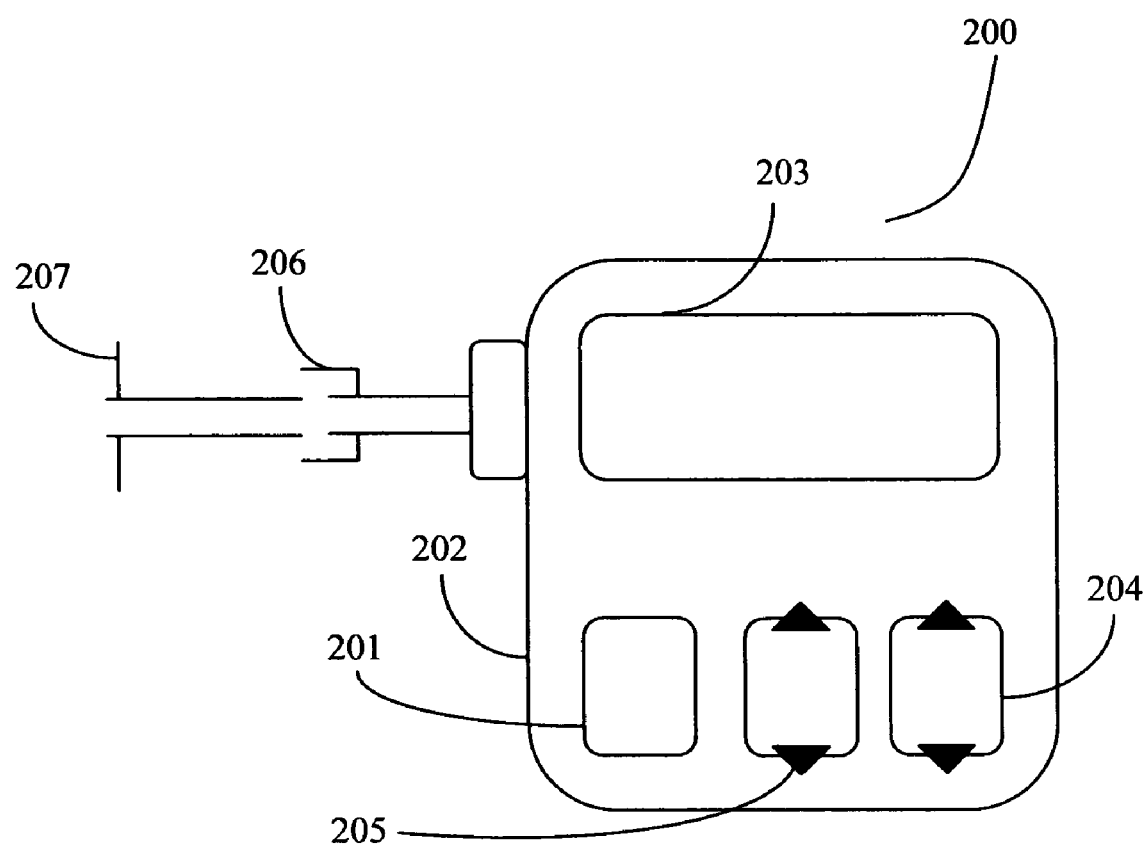
FIG. 2A illustrates the top view of the pericardium meridian stimulator when strapped on the ventral side of the patient's wrist.

FIG. 2A illustrates the top view of the pericardium meridian stimulator 200 as seen by the patient when the pericardium meridian stimulator is strapped onto the wrist of the patient. The pericardium meridian stimulator 200 is provided with a female connector 206 and male connector 207 for the wire-line connection from the battery to the electrodes, and a liquid crystal display (LCD) 203 read out located on the upper face of the pericardium meridian stimulator 200 in view of the patient. The LCD 203 displays the current supplied to the electrodes 101 and 102 and for indicating via an indicator light when electric power is being supplied to the electrodes 101 and 102. The LCD 203 touch screen 202 interface is provided with a power on-off button 201 and a switch 205 for increasing the electric pulse rate and thereby the electrical stimulation rate. The LCD 203 displays the current supplied to the electrodes. The power supplied to the electrodes 101 and 102 from the local battery is a low ampere, low voltage current, for example a 10, 20 or 30 milliampheres at 3 volts. The touch screen 202 button 204 increases or decreases the stimulus signal at the PC 6 and PC 7 points by increasing or decreasing the current flow from the local battery to the electrodes 101 and 102. The LCD 203 also displays the pattern of current flowing between the electrodes, for example the electric pulse interval. The electric pulse rate is adjustable by an oscillator contained in the pericardium meridian stimulator 200 housing. The electric pulse rate can be adjusted by the patient or the medical practitioner using button 205 on the touch screen 202 from about 0.1 hertz to about 10 hertz For example, using button 205, the patient can set the cycle frequency at 1 hertz and receive a 1 pulse per second stimulus at the PC 6 point and the PC 7 point. The current flow through the electrodes 101 and 102 also produces an audible beep or click at the pericardium meridian stimulator. An audible disconnect alarm is provided in the electronic circuit of the pericardium meridian stimulator 200.

The electric circuit of the pericardium meridian 200 can output either a continuous current, or a pulsed current to the positive electrode 101 and the negative electrode 102 positioned at the PC 7 and PC 6 points respectively. The electrically insulated base of the pericardium meridian stimulator 200 and the electrically insulated material of the straps 105 ensure that the only path for the current flow in the now closed output circuit from the positive electrode 101 to the negative electrode 102 through the flesh of the wrist along the pericardium meridian. In general, increasing the current amperage using button 204, or increasing the electric pulse rate using button 205 up to a certain point increases the anti-nausea effect of the invention.

Figure 2B:
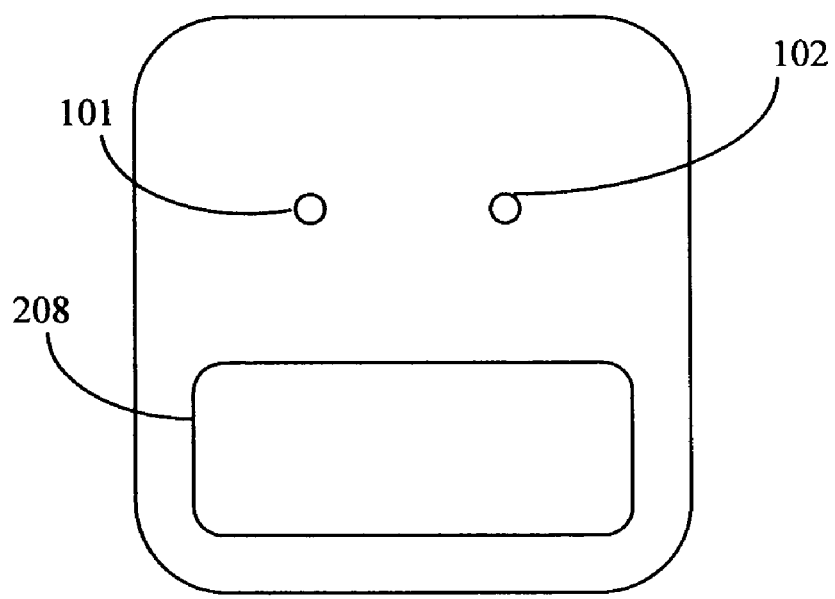
FIG. 2B illustrates the bottom view of the pericardium meridian stimulator. The bottom surface is in contact with the patient's wrist.

FIG. 2B illustrates the lower surface view of the pericardium meridian stimulator. The electrode assembly is detachably attached to the lower surface of the housing and is adapted for contact with the ventral side of the wrist of the patient. The electric circuitry in the pericardium meridian stimulator 200 is powered by the local battery source 208 located in the housing of the stimulator 200. The local battery 208 is a low voltage battery, for example, a 3 volt or 9 volt battery.

Figure 3:
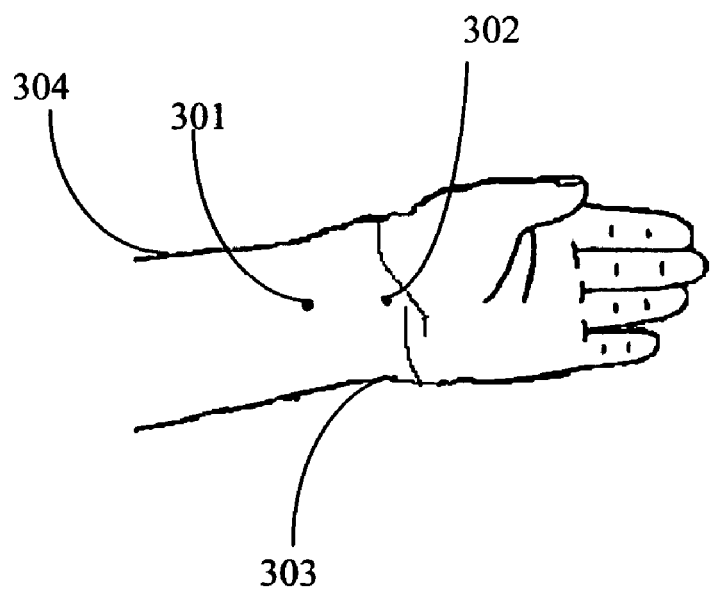
FIG. 3 illustrates the pericardium meridian six (PC 6) acupuncture point and pericardium meridian seven (PC 7) acupuncture point on the ventral side of the patient's wrist.

FIG. 3 illustrates the position of pericardium meridian six point 301 (PC 6) and the pericardium meridian seven point 302 (PC 7) on the ventral side of the patient's 304 wrist 303. The positive electrode 101 is positioned at the PC 7 point and the negative electrode 102 is positioned at the PC 6 point prior to passage of the electric power through the electrodes.

Figure 4:
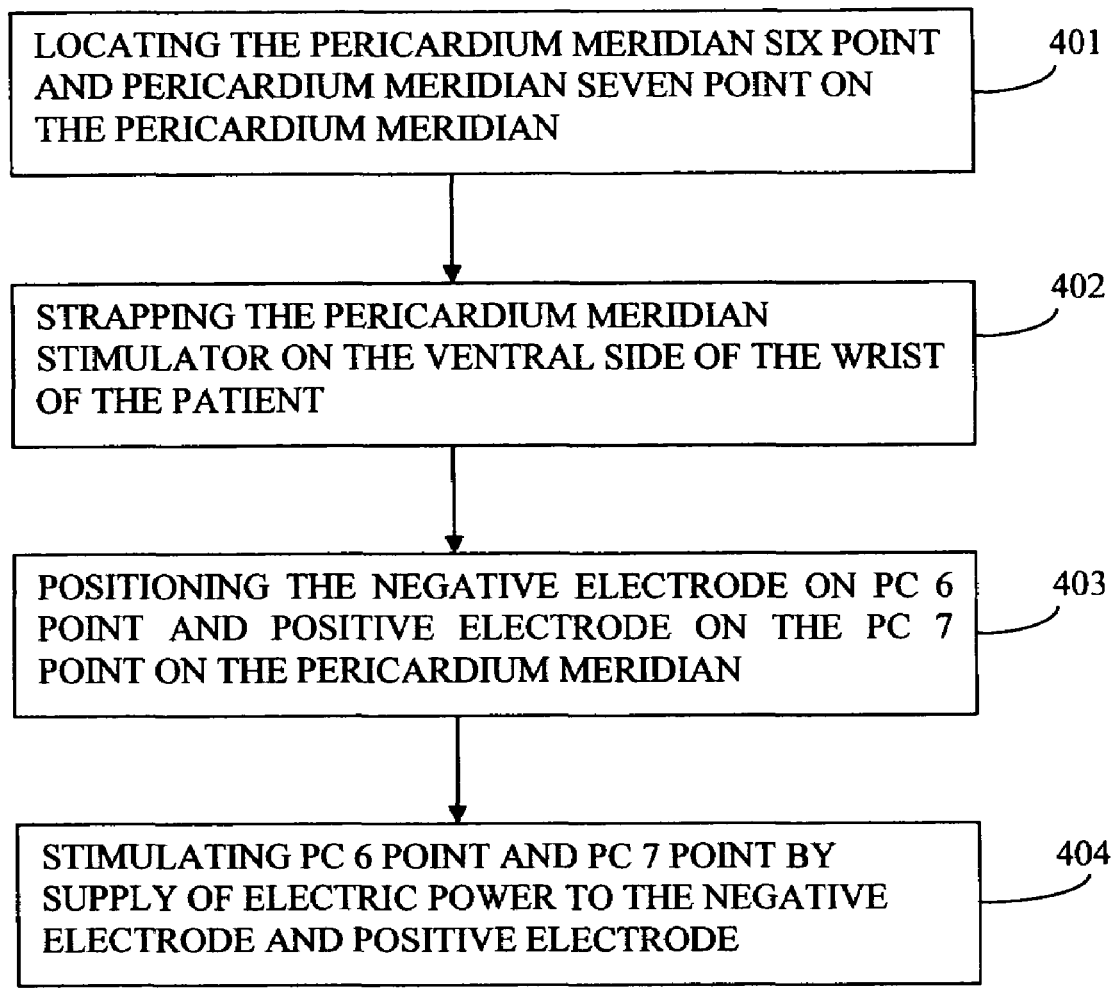
FIG. 4 illustrates the method of applying electro-acupuncture at the PC 6 and PC 7 pericardium meridian acupuncture points.

FIG. 4 illustrates the method of applying electro-acupuncture at the pericardium meridian six point and the pericardium meridian seven point. The pericardium meridian six point and the pericardium seven point is located on the ventral side of the patient's 304 wrist 303. The pericardium meridian stimulator is strapped 402 onto the wrist 303 of the patient 304. The negative electrode 102 is positioned on the pericardium meridian point six and the positive electrode 101 is positioned on the pericardium meridian seven point by adjusting 402 the distance between the electrodes along a guide or track housed in the wrist band housing. A continuous or pulsed current of selected amplitude is applied to the positive electrode 101 and to the negative electrode 102, whereby the pericardium six point (PC 6) and the pericardium seven point (PC 7) is simultaneously stimulated 404 along the pericardium meridian.

Figure 5:
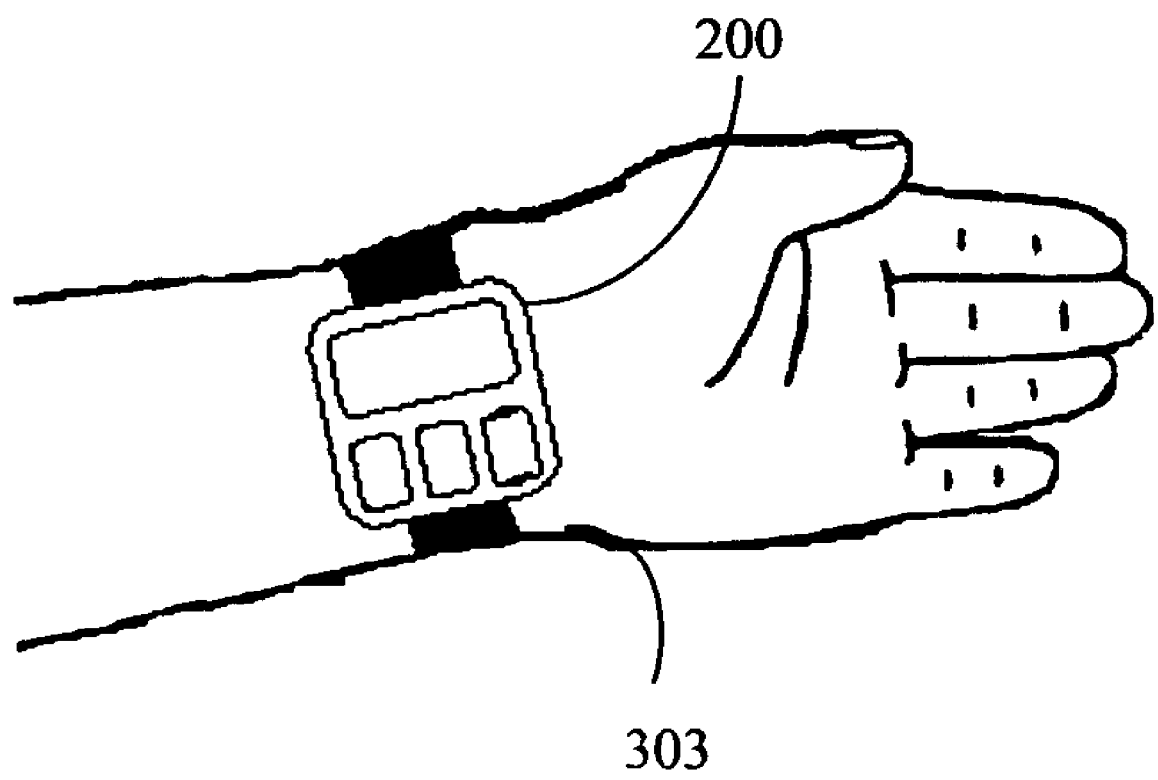
FIG. 5 illustrates the position of the pericardium meridian stimulator device on the ventral side of the patient's wrist.

FIG. 5 illustrates shows the pericardium meridian stimulator 200 strapped on the ventral side of the patient's wrist 303. The simultaneous electrical stimulation of both the PC 6 point 301 and PC 7 point 302 is much more effective in prevention and treatment of nausea and vomiting compared to the stimulus of only one point, such as PC 6 301. The simultaneous stimulation of both PC 6 301 and PC 7 302 helps in the prevention and treatment of nausea and vomiting induced by general anesthesia and by medication, for example, narcotic pain alleviation drugs and chemotherapy. The pericardium meridian stimulator system of this invention can also be used to treat vertigo, dizziness, tinnitus, motion sickness and similar conditions.

The simultaneous electro-stimulation procedure at the PC 6 and PC 7 acupuncture point, described above, has been used to effectively treat patients considered high risk for post-operative nausea and vomiting, for example, in procedures such as laparoscopies, sinus surgeries, thyroidectomy, etc. The simultaneous PC 6 and PC 7 electro-stimulation procedure of this invention has also been used to treat patients who have a history of severe post-opeartive nausea and vomiting after receiving general anesthesia, and for patients who developed severe post-operative nausea and vomiting in the post-anesthetic recovery room and failed to respond to conventional medical therapies, for example the administration of drugs such as Metoclopromide and/or Ondansetron.

What is claimed is:

1. A method of controlling nausea and vomiting in a patient using a pericardium meridian stimulator comprising a negative electrode and a positive electrode, said electrodes housed in a wrist band-type apparatus, said method comprising the steps of:
   locating the pericardium meridian six point and the pericardium meridian seven point on the ventral side of the wrist of the patient, wherein the distance between said points varies among patients;
   positioning the negative electrode on the pericardium meridian six point and adjusting the distance of the positive electrode from the negative electrode to position said positive electrode on the pericardium meridian seven point, and,
   delivering electric power simultaneously at the pericardium meridian six point and at the pericardium meridian seven point through the negative electrode and the positive electrode respectively, wherein the power supplied to the electrodes is displayed on a monitor of a liquid crystal display whereby an electro-generated stimulus is generated along the pericardium meridian between the pericardium six point and the pericardium seven point.

2. A pericardium meridian stimulator for prevention and treatment of nausea and vomiting by simultaneous electrical stimulation of the pericardium meridian six point and the pericardium meridian seven point on the ventral side of the wrist of a patient, said pericardium meridian stimulator comprising:
   a wrist-band like housing worn on the ventral side of the human wrist; said wrist band housing having an outer surface and an inner surface, said inner surface adapted to be applied to the ventral side of the wrist of the patient;
   an electrode assembly detachably attached to the inner surface of the housing and adapted for contact with the ventral side of the wrist of the patient; said electrode assembly comprising a negative electrode and a positive electrode;
   an electric circuitry connected to said electrodes;
   a liquid crystal display with a touch screen mechanism; and,
   a distance adjustment means in said housing for adjusting the distance between the negative electrode and the positive electrode along a longitudinal axis parallel to a patient's arm on the ventral side of the wrist of the patient, to allow the negative electrode to be positioned on the meridian six point and the positive electrode to be positioned on the meridian seven point.

3. The pericardium meridian stimulator of claim 2, wherein the electric circuitry is selectively operable by the patient.

4. The pericardium meridian stimulator of claim 2, wherein said electric circuitry includes means for producing audible clicks proportional to the electrical power supplied to the electrodes.

5. The pericardium meridian stimulator of claim 2, wherein said liquid crystal display indicates via an indicator light when power is being supplied to the negative electrode and to the positive electrode.

6. The pericardium meridian stimulator of claim 2, wherein said liquid crystal display is provided with a touch screen for turning power on or off to the negative electrode and positive electrode.

7. The electric circuitry of claim 2, wherein an electric pulse rate to the patient is adjustable using said touch screen mechanism of the liquid crystal display.

8. The pericardium meridian stimulator of claim 2, wherein the electric circuitry powers the liquid crystal display in the housing for displaying the current supplied to the negative electrode and the positive electrode.

9. The pericardium meridian stimulator of claim 2, wherein the electric circuitry and electrodes are powered by a battery source.

10. The pericardium meridian stimulator of claim 2, wherein a disposable sheath is provided over the negative electrode and the positive electrode.

11. The pericardium meridian simulator of claim 10, wherein said disposable sheath is composed of a highly conducting material.

12. The pericardium meridian stimulator of claim 2, wherein the electric power supplied to the negative electrode and the positive electrode is pulsed.

13. The pericardium meridian stimulator of claim 2, wherein the electric power supplied to the negative electrode and to the positive electrode is continuous.

14. The pericardium meridian stimulator of claim 2, wherein the negative electrode and the positive electrode are detachably attached to the housing.

* * * * *